United States Patent [19]

Viebach et al.

[11] Patent Number: 5,209,222

[45] Date of Patent: May 11, 1993

[54] ULTRASONIC TRANSDUCER IN LITHOTRIPTERS

[75] Inventors: Thomas Viebach, Paehl; Roland Denk, Munich; Alexander Heese, Munich; Anton Haas, Munich; Rainer Kreibich, Munich, all of Fed. Rep. of Germany

[73] Assignee: Dornier Medizintechnik GmbH, Fed. Rep. of Germany

[21] Appl. No.: 632,102

[22] Filed: Dec. 19, 1990

[30] Foreign Application Priority Data

Dec. 21, 1989 [DE] Fed. Rep. of Germany ....... 3942253

[51] Int. Cl.$^5$ ............................................. A61B 17/22
[52] U.S. Cl. .......................... 128/24 OEL; 128/660.03
[58] Field of Search ......... 128/24 AA, 24 EL, 660.03

[56] References Cited

U.S. PATENT DOCUMENTS

| 4,901,709 | 2/1990 | Rattner | 128/24 EL |
|---|---|---|---|
| 4,915,114 | 4/1990 | Hassler | 128/24 EL |
| 4,928,672 | 5/1990 | Grasser et al. | 128/24 EL |
| 4,947,830 | 8/1990 | Rattner et al. | 127/24 EL |
| 4,957,099 | 9/1990 | Hassler | 128/660.03 |
| 4,984,565 | 1/1991 | Rattner et al. | 128/24 EL |
| 5,009,232 | 4/1991 | Hassler et al. | 128/24 EL |
| 5,025,789 | 6/1991 | Hassler | 128/24 EL |
| 5,031,626 | 7/1991 | Hassler et al. | 128/24 EL |

FOREIGN PATENT DOCUMENTS

| 0312847 | 4/1989 | European Pat. Off. | 128/24 EL |
|---|---|---|---|
| 8863299 | 6/1988 | Fed. Rep. of Germany | 128/24 EL |
| 3727692 | 3/1989 | Fed. Rep. of Germany | 128/24 EL |

*Primary Examiner*—Lee S. Cohen
*Assistant Examiner*—K. M. Pfaffle
*Attorney, Agent, or Firm*—Ralf H. Siegemund

[57] ABSTRACT

A lithotripter having a shockwave generator having a cavity filled with water, further having an ultrasonic, locating transducer mounted by means of a holding device which includes metallic inner and outer shells each having a large acoustic impedance as compared with water and an acoustically attenuating layer interposed between the two shells; the shells are spaced from each other so that the shockwaves will be eliminated by interference.

2 Claims, 1 Drawing Sheet

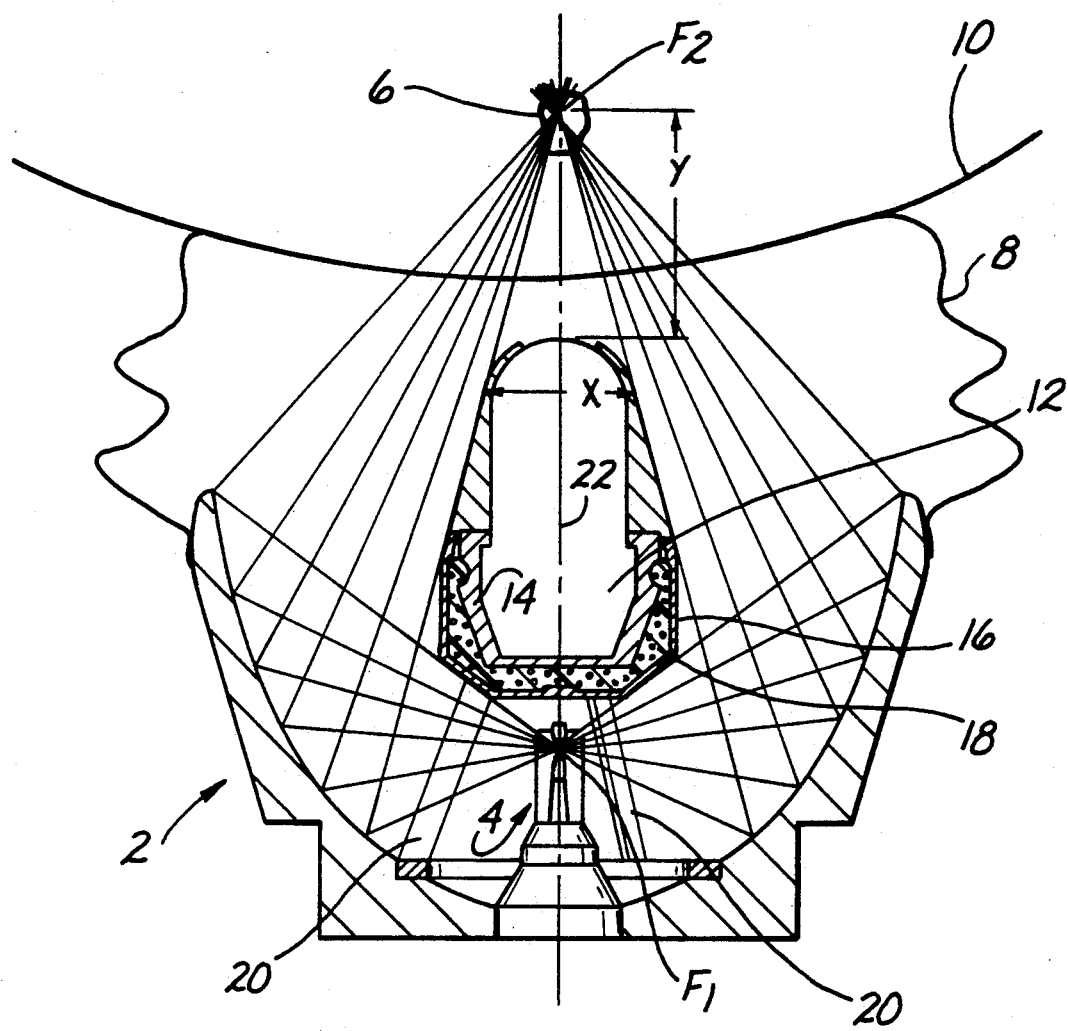

ULTRASONIC TRANSDUCER IN LITHOTRIPTERS

BACKGROUND OF THE INVENTION

The present invention relates to an ultrasonic transducer which is positioned within the cavity of a water filled shockwave generator, to be used in conjunction with lithotripsy, the transducer being provided for diagnosis generally, to respond (e.g. locate) to concrements of in the body of a living being.

Transducers of the kind referred to above are known and mentioned for example in the book "End of the Stone Age", London 1987. Transducers of this kind are used in conjunction with shockwave generators using an arc discharge or in the case of electromagnetically produced shockwaves with a piezoceramic areal shockwave source.

DESCRIPTION OF THE INVENTION

It is an object of the present invention to provide a new and improved positioning of such ultrasonic transducer within the cavity and aperture zone of a shockwave generator, and to reduce the load on that transducer whenever being exposed to the production of shockwaves, to thereby increase the use life of that transducer, and thus of the equipment as a whole.

In accordance with the preferred embodiment of the present invention it is suggested to provide a holder for the transducer within the water filled aperture opening by means of a two shell body that acts as attenuator and interference filter. Specifically the two shell body has a metallic outer shell, a metallic inner shell each having a large acoustic impedance difference with regard to water, and a sound absorbing (attenuating) layer is interposed having also a highly different acoustic impedance as far as the acoustic impedance of the metal used for the shell is concerned. In a preferred embodiment it is suggested to provide such a thickness so that the shockwaves at the frequency of maximum intensity are eliminated by interference.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

The FIGURE illustrats an example of the preferred embodiment of the present invention in cross section and under conditions which are deemed to be the best mode of practicing the invention.

The FIGURE shows a known shockwave generator which includes a reflector 2 which is a portion of a rotational ellipsoid defined by the thus configured contour of the inner surface of a body 5. The ellipsoid is truncated, i.e. it is open at one end. An arc discharge is provided in the focal point F1 of this rotational ellipsoid by means of a set of electrodes 4. Specifically, the arc discharge is established through a gap between two electrodes. Structures of this type are shown e.g. in U.S. Pat. Nos. 4,809,682; 4,940,050.

The rotational ellipsoid, by virtue of the geometry involved, has a second focal point F2 and the entire arrangement is positioned so that this second point F2 coincides with a concrement 6 within the body of a person. The person is identified by the reference character P and reference numeral 10 refers to the outer skin of that patient. The rotational ellipsoid is closed with a membrane sac 8 which is also filled with water and is placed into abutment with the skin 10 of the patient.

The equipment includes an ultrasonic transducer 12 which has an "open" output 13 that is directed towards the concrement. The particular configuration therefore is one of physical combination of a diagnostic and locating device 12 by means of which the concrement 6 is located, and of a treatment device and therapeutic head of which body 5 is a part.

As can be seen the transducer 12 is situated generally within the shockwave field. It does not provide too much of a shading of generated shockwave (see below) because the construction is such that the transducer 12 would be exposed to unreflected and unfocussed shockwaves. The others run more or less around the transducer 12 so that there is no significant loss in shockwave energy. On the other hand there is of course a significant exposure of the transducer 12 to shockwave energy as such and the attenuation of the effect of such shockwave on the equipment is the task at hand and solved by the inventive holder for the transducer 12.

The holder 15 under consideration includes a two shell configuration with an inner shell 14 and an outer shell 16. They are identified through different shadings of the metal. They are indeed made of metal, and metal has usually a very hard large impedance as compared with the acoustic impedance of water. The two shells 16 and 14 are separated by a space and that space is filled with an attenuating medium 18. This attenuating medium may be a foamed synthetic generally or rubber or silicon caoutchouc.

As far as the shockwaves produced by the shockwave generator 4 are concerned, four different boundaries or interfaces are established in relation to the transducer 12 and involving media with strongly different acoustic impedance. The inner shell 14 is decoupled from the outer shell 16 and from the connection 20 of the holder 15 to the body 5. Any shockwave has to traverse the following boundaries defined by interfaces of material with significantly differing acoustic impedances.

The shockwaves have to pass four interfaces. A first interface is the area of contact of the waterwith the metal on the outer surfaces of the shell 16. The second interface is set up between the metal of the outer shell 16 and the attenuating medium 18. The third interface is the area of contact between the attenuating medium 18 and the inner shell 14 and the forth interface is between the shells and the transducer body 12 itself.

All these four interfaces are defined as differences in the acoustic impedance. In each instance the shockwave is partially reflected which of course leads already to a strong attenuation of any wave energy that can reach the interior of transducer 12.

The thickness of the layer 18 is selected so that the frequency portion of the shockwave spectrum in addition with a maximum intensity is attenuated through interference. On the other hand a high internal attenuation of the attenuating medium 18 obtains by using e.g. a blend of a two component Si or by operation of many microspheres or hollow glass spheres. Attenuation results from the multiple statistically distributed synthetic-gas interfaces and owing to the smallness one can say that the shockwave fronts are diffusely reflected i.e. scattered within that attenuating medium.

The ultrasonic transducer 12 serves for the locating of the concrement and, therefore, it must be absolutely certain that its center axis 22 is continuously directed towards the concrement i.e. the axis 22 which is a center axis of the transducer 12 as such must always remain through the two focal points F1 and F2 of the ellipsoid. This condition is assured only if in fact the holders 15 and 20 of the transducer can guarantee its position even under the influence of shockwave energy. The particular material as selected for attenuation must be such that its mechanical stiffness provides a form stable embedment of the online transducer, and even in the case of direct coupling to the patient body, no interfering shifts and deformations in the locating system obtain.

As far as construction is concerned care is being taken that the shading of the reflected shockwaves through the inline transducer holding device is minimized. The outer contour of the holder 15 is basically given by the diameter X of the transducer itself, and there is a distance Y from the therapeutic focus F2. These are the parameters of importance, and the shockwave is, in a waveguide fashion, guided along this holding jacket for the transducer. The shockwave front runs more or less perpendicular to that protective jacket and there are small reflections and a minimal refraction, so that the shockwave as it bypasses the transducer is in fact attenuated to a limited extent which is the desired result.

The shading of some of the shockwaves particularly those near the aperture and near the rotational axis 22 of the ellipsoid really eliminates phase incorrect shockwave portions and those that do not give optimal reflection, these are waves from the electrode area that are not focussed. Thus, the shading actually enhances and improves the overall focussing and concentration of shockwaves as compared with no online holding equipment. The so called primary shockwave (not focussed) are actually completely eliminated by the online holding device and that is certainly a desired result.

The invention is not limited to the embodiments described above but all changes and modifications thereof, not constituting departures from the spirit and scope of the invention, are intended to be included.

We claim:

1. In a lithotripter which includes a shockwave generator having a cavity which is filled with water, the lithotripter further including an ultrasonic locating transducer and a holding device for the transducer, the holding device being positioned in an area and zone of propagation of shockwaves, said shockwaves as produced by the transducer having a particular frequency spectrum with a particular maximum frequency of emission, the improvement of the holding device, comprising:

a metallic outer shell;

a metallic inner shell;

each of the shells having a large acoustic impedance as compared with water; and an acoustically attenuating layer in between the two shells and having by itself an acoustic impedance being different from the acoustic impedance of the the metallic shells.

2. Lithotripter as in claim 1, the attenuating layer having a thickness so that the particular maximum frequency of the shockwave spectrum having a maximum intensity will in fact be eliminated due to interference effective across the attenuating layer between the inner and outer shells.

* * * * *